United States Patent
Allen, IV et al.

(10) Patent No.: US 12,251,155 B2
(45) Date of Patent: Mar. 18, 2025

(54) METHODS FOR OPEN DISSECTION USING SEALING INSTRUMENT

(71) Applicant: Covidien LP, Mansfield, MA (US)

(72) Inventors: James D. Allen, IV, Broomfield, CO (US); William D. Faulkner, Boulder, CO (US); Duane E. Kerr, Loveland, CO (US)

(73) Assignee: Covidien LP, Mansfield, MA (US)

( * ) Notice: Subject to any disclaimer, the term of this patent is extended or adjusted under 35 U.S.C. 154(b) by 554 days.

(21) Appl. No.: 17/331,812

(22) Filed: May 27, 2021

(65) Prior Publication Data

US 2022/0378494 A1    Dec. 1, 2022

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1206* (2013.01); *A61B 2018/00601* (2013.01); *A61B 2018/00702* (2013.01); *A61B 2018/00714* (2013.01); *A61B 2018/00875* (2013.01)

(58) Field of Classification Search
CPC ............ A61B 18/1445; A61B 18/1206; A61B 2018/00601; A61B 2018/00702; A61B 2018/00714; A61B 2018/00875
See application file for complete search history.

(56) References Cited

U.S. PATENT DOCUMENTS

| | | |
|---|---|---|
| 2,068,721 A | 1/1937 | Wappler |
| 4,091,813 A | 5/1978 | Shaw et al. |
| 5,389,098 A | 2/1995 | Tsuruta et al. |
| 5,403,312 A | 4/1995 | Yates et al. |
| 5,465,895 A | 11/1995 | Knodel et al. |
| 5,810,811 A | 9/1998 | Yates et al. |
| 5,827,271 A | 10/1998 | Buysse et al. |
| 5,833,690 A | 11/1998 | Yates et al. |
| 5,876,401 A | 3/1999 | Schulze et al. |
| 5,911,719 A | 6/1999 | Eggers |
| 6,024,741 A | 2/2000 | Williamson, IV et al. |

(Continued)

FOREIGN PATENT DOCUMENTS

| | | |
|---|---|---|
| EP | 2754403 A2 | 7/2014 |
| EP | 3087941 A1 | 11/2016 |
| EP | 3222239 A1 | 9/2017 |

OTHER PUBLICATIONS

International Search Report and Written Opinion for application No. PCT/IB2022/054323 mailed Aug. 10, 2022.

(Continued)

*Primary Examiner* — Daniel W Fowler
*Assistant Examiner* — Annie L Shoulders

(57) ABSTRACT

An electrosurgical system includes jaw members having a cutting element extending therebetween and a generator configured to: provide minimal power to the cutting element to maintain a pre-dissection temperature thereof; sense a change in resistance of the cutting element and ramp up power to a dissection temperature; regulate the temperature of the cutting element by regulating power; and terminate power to the cutting element to allow the cutting element to cool to the pre-dissection temperature before providing power back to the cutting element.

15 Claims, 15 Drawing Sheets

(56) References Cited

U.S. PATENT DOCUMENTS

| | | | |
|---|---|---|---|
| 6,086,586 | A | 7/2000 | Hooven |
| 6,273,887 | B1 | 8/2001 | Yamauchi et al. |
| 6,402,747 | B1 | 6/2002 | Lindemann et al. |
| 6,602,252 | B2 | 8/2003 | Mollenauer |
| 6,736,813 | B2 | 5/2004 | Yamauchi et al. |
| 6,776,780 | B2 | 8/2004 | Mulier et al. |
| 6,802,843 | B2 | 10/2004 | Truckai et al. |
| 6,808,525 | B2 | 10/2004 | Latterell et al. |
| 6,821,273 | B2 | 11/2004 | Mollenauer |
| 6,860,880 | B2 | 3/2005 | Treat et al. |
| 6,899,710 | B2 | 5/2005 | Hooven |
| 6,929,641 | B2 | 8/2005 | Goble et al. |
| 6,953,461 | B2 | 10/2005 | McClurken et al. |
| 7,011,656 | B2 | 3/2006 | McGaffigan et al. |
| 7,033,356 | B2 | 4/2006 | Latterell et al. |
| 7,070,597 | B2 | 7/2006 | Truckai et al. |
| 7,083,619 | B2 | 8/2006 | Truckai et al. |
| 7,112,201 | B2 | 9/2006 | Truckai et al. |
| 7,125,409 | B2 | 10/2006 | Truckai et al. |
| 7,147,637 | B2 | 12/2006 | Goble |
| 7,169,146 | B2 | 1/2007 | Truckai et al. |
| 7,204,835 | B2 | 4/2007 | Latterell et al. |
| 7,270,664 | B2 | 9/2007 | Johnson et al. |
| 7,276,068 | B2 | 10/2007 | Johnson et al. |
| 7,326,202 | B2 | 2/2008 | McGaffigan |
| 7,329,255 | B2 | 2/2008 | McGaffigan |
| 7,354,440 | B2 | 4/2008 | Truckai et al. |
| 7,357,802 | B2 | 4/2008 | Palanker et al. |
| 7,364,577 | B2 | 4/2008 | Wham et al. |
| 7,396,356 | B2 | 7/2008 | Mollenauer |
| 7,419,490 | B2 | 9/2008 | Falkenstein et al. |
| 7,686,827 | B2 | 3/2010 | Hushka |
| 7,815,641 | B2 | 10/2010 | Dodde et al. |
| 7,931,649 | B2 | 4/2011 | Couture et al. |
| 8,034,051 | B2 | 10/2011 | Martin et al. |
| 8,162,940 | B2 | 4/2012 | Johnson et al. |
| 8,187,273 | B2 | 5/2012 | Kerr et al. |
| 8,197,472 | B2 | 6/2012 | Lau et al. |
| 8,226,649 | B2 | 7/2012 | Falkenstein et al. |
| 8,292,879 | B2 | 10/2012 | Manwaring et al. |
| 8,303,585 | B2 | 11/2012 | Mollenauer |
| 8,372,066 | B2 | 2/2013 | Manwaring et al. |
| 8,377,052 | B2 | 2/2013 | Manwaring et al. |
| 8,394,094 | B2 | 3/2013 | Edwards et al. |
| 8,425,503 | B2 | 4/2013 | Manwaring et al. |
| 8,491,578 | B2 | 7/2013 | Manwaring et al. |
| 8,491,626 | B2 | 7/2013 | Roy et al. |
| 8,523,850 | B2 | 9/2013 | Manwaring et al. |
| 8,523,852 | B2 | 9/2013 | Manwaring et al. |
| 8,551,088 | B2 | 10/2013 | Falkenstein et al. |
| 8,562,598 | B2 | 10/2013 | Falkenstein et al. |
| 8,568,411 | B2 | 10/2013 | Falkenstein et al. |
| 8,597,293 | B2 | 12/2013 | Falkenstein et al. |
| 8,597,297 | B2 | 12/2013 | Couture et al. |
| 8,617,151 | B2 | 12/2013 | Denis et al. |
| 8,623,003 | B2 | 1/2014 | Lau et al. |
| 8,636,730 | B2 | 1/2014 | Keppel |
| 8,734,445 | B2 | 5/2014 | Johnson et al. |
| 8,915,909 | B2 | 12/2014 | Manwaring et al. |
| 8,932,279 | B2 | 1/2015 | Stringham et al. |
| 8,951,248 | B2 | 2/2015 | Messerly et al. |
| 9,005,199 | B2 | 4/2015 | Beckman et al. |
| 9,039,694 | B2 | 5/2015 | Ross et al. |
| 9,050,100 | B2 | 6/2015 | Yates et al. |
| 9,084,606 | B2 | 7/2015 | Greep |
| 9,131,977 | B2 | 9/2015 | Manwaring et al. |
| 9,149,321 | B2 | 10/2015 | Stringham et al. |
| 9,192,427 | B2 | 11/2015 | Johnson et al. |
| 9,265,553 | B2 | 2/2016 | Manwaring et al. |
| 9,265,554 | B2 | 2/2016 | Manwaring et al. |
| 9,265,555 | B2 | 2/2016 | Manwaring et al. |
| 9,265,556 | B2 | 2/2016 | Manwaring et al. |
| 9,320,560 | B2 | 4/2016 | Manwaring et al. |
| 9,387,037 | B2 | 7/2016 | Yang |
| 9,402,679 | B2 | 8/2016 | Ginnebaugh et al. |
| 9,579,146 | B2 | 2/2017 | Johnson et al. |
| 9,918,774 | B2 | 3/2018 | Batchelor et al. |
| 9,931,157 | B2 | 4/2018 | Strobl et al. |
| 9,955,858 | B2 | 5/2018 | Pamnani et al. |
| 10,085,794 | B2 | 10/2018 | Kerr et al. |
| 10,204,773 | B2 | 2/2019 | Sugiyama et al. |
| 10,213,247 | B2 | 2/2019 | Manwaring et al. |
| 2007/0135808 | A1 | 6/2007 | Kupferschmid et al. |
| 2007/0265616 | A1 | 11/2007 | Couture et al. |
| 2008/0086195 | A1 | 4/2008 | Atanasoka et al. |
| 2011/0077630 | A1 | 3/2011 | Tanaka et al. |
| 2012/0226270 | A1 | 9/2012 | Manwaring et al. |
| 2013/0066310 | A1* | 3/2013 | Manwaring ............ A61B 18/10 606/29 |
| 2014/0135804 | A1 | 5/2014 | Weisenburgh, II et al. |
| 2016/0310207 | A1* | 10/2016 | Honda ............... A61B 18/1445 |
| 2017/0156788 | A1 | 6/2017 | Johnson et al. |
| 2017/0196648 | A1 | 7/2017 | Ward et al. |
| 2017/0245923 | A1* | 8/2017 | Takashino ............ A61B 18/085 |
| 2017/0252087 | A1* | 9/2017 | Takashino ............. A61B 18/10 |
| 2018/0303322 | A1 | 10/2018 | Pamnani et al. |
| 2019/0000538 | A1 | 1/2019 | Widenhouse et al. |
| 2019/0262062 | A1 | 8/2019 | Akagane |
| 2019/0274708 | A1* | 9/2019 | Boudreaux ......... A61B 17/3211 |
| 2020/0030020 | A1* | 1/2020 | Wang ................. A61B 18/1445 |

OTHER PUBLICATIONS

Gnedenkov et al., "Magnesium fabricated using additive technology: Specificity of corrosion and protection", Journal of Alloys and Compounds, Elsevier, vol. 808, Jul. 29, 2019, XP085792710.

International Search Report and Written Opinion issued in corresponding International Application No. PCT/US2020/061998 mailed Mar. 22, 2021, 14 pages.

* cited by examiner

METHODS FOR OPEN DISSECTION USING SEALING INSTRUMENT

FIELD

The present disclosure relates to methods of surgical instruments and systems for cutting tissue and, more particularly, to methods of using a surgical sealing instrument having an electrical or cutting element for dissecting tissue.

BACKGROUND

A surgical forceps is a pliers-like instrument that relies on mechanical action between its jaw members to grasp, clamp, and constrict tissue. Electrosurgical forceps utilize both mechanical clamping action and energy to heat tissue to treat, e.g., coagulate, cauterize, or seal, tissue. Typically, once tissue is treated, the surgeon has to accurately sever the treated tissue. Accordingly, many electrosurgical forceps are designed to incorporate a knife that is advanced between the jaw members to cut the treated tissue. As an alternative to a mechanical knife, an energy-based tissue cutting element may be provided to cut the treated tissue using energy, e.g., thermal, electrosurgical, ultrasonic, light, or other suitable energy.

When dissecting tissue, a surgeon typically relies on a second surgical instrument which is substituted or used in conjunction with the sealing instrument to dissect tissue. With certain sealing instruments, the two opposing jaw members may be opened and the jaw member having the electrical or thermal cutting element may be utilized to dissect tissue. When utilizing this technique, various algorithms need to be employed to control the flow of electrical energy to the electrical or thermal cutter to avoid inadvertently heating adjacent tissue.

SUMMARY

As used herein, the term "distal" refers to the portion that is being described which is farther from an operator (whether a human surgeon or a surgical robot), while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, design variations, and/or other variations, up to and including plus or minus 10 percent. Further, to the extent consistent, any or all of the aspects detailed herein may be used in conjunction with any or all of the other aspects detailed herein.

Provided in accordance with aspects of the present disclosure is an electrosurgical system that includes first and second jaw members each defining a tissue treating surface. The first and second jaw members are pivotably coupled to one another such that either of the first or second jaw members is movable relative to the other from a spaced-apart position to an approximated position to grasp tissue between the tissue treating surfaces. The tissue treating surfaces are adapted to connect to a source of energy to treat tissue grasped therebetween. One of the first or second jaw members includes a thermal cutting element extending from the tissue treating surface thereof.

A generator electrically is coupled to the first and second jaw members and is configured to provide electrical energy thereto to produce a tissue seal between the jaw members upon activation of a first switch and is configured to openly dissect tissue with the thermal cutting element upon activation of a second switch. The generator, upon continued activation of the second switch, is configured to: provide minimal power to the cutting element to maintain a pre-dissection temperature of the cutting element; sense a change in power to maintain the cutting element resistance or change in resistance of the cutting element reflective of tissue contact with the cutting element and ramp up power until the cutting element reaches a dissection temperature; regulate power to maintain the temperature of the cutting element at the dissection temperature during open dissection; and terminate power to the cutting element upon release of the second switch to allow the cutting element to cool to the pre-dissection temperature before providing power to the cutting element upon re-activation of the second switch.

In aspects according to the present disclosure, the generator is configured to maintain a pre-dissection temperature of the cutting element in the range of about 20° C. to about 60° C.

In aspects according to the present disclosure, upon detection of the cutting element contacting tissue, the generator is ramped up to a dissection temperature of about 550° C. In other aspects according to the present disclosure, the generator is configured to regulate the power to maintain the cutting element at the dissection temperature of about 550° C. during open dissection.

In aspects according to the present disclosure, the generator is configured to terminate power to the cutting element upon release of the second switch to allow the cutting element to cool back to the pre-dissection temperature in the range of about 20° C. to about 60° C. before providing power to the cutting element upon re-activation of the second switch.

In aspects according to the present disclosure, power to the cutting element is only provided when the jaw members are disposed in the spaced-apart position and the second switch is activated.

Provided in accordance with other aspects of the present disclosure is an electrosurgical system that includes first and second jaw members each defining a tissue treating surface. The first and second jaw members are pivotably coupled to one another such that either of the first or second jaw members is movable relative to the other from a spaced-apart position to an approximated position to grasp tissue between the tissue treating surfaces. The tissue treating surfaces are adapted to connect to a source of energy to treat tissue grasped therebetween. One of the first or second jaw members includes a thermal cutting element extending from the tissue treating surface thereof.

A generator electrically is coupled to the first and second jaw members and is configured to provide electrical energy thereto to produce a tissue seal between the jaw members upon activation of a first switch and is configured to openly dissect tissue with the thermal cutting element upon activation of a second switch. The generator, upon continued activation of the second switch, is configured to: provide minimal power to the cutting element to maintain a pre-dissection temperature of the cutting element; sense a change in power to maintain the cutting element resistance or change in resistance of the cutting element reflective of tissue contact with the cutting element and ramp up power until the cutting element reaches a dissection temperature; regulate power to maintain the temperature of the cutting element at the dissection temperature during open dissection; upon loss of contact of the cutting element with tissue during open dissection with the second switch activated, reduce power to the cutting element; sense a subsequent change in power to maintain the cutting element resistance or change in resistance of the cutting element reflective of tissue reinitiating contact with the cutting element and ramp up power until the cutting element reaches the dissection temperature; regulate power to maintain the temperature of the cutting element at the dissection temperature during continued open dissection; and terminate power to the cutting element upon release of the second switch to allow the cutting element to cool to the pre-dissection temperature before providing power to the cutting element upon re-activation of the second switch.

In aspects according to the present disclosure, the generator is configured to maintain a pre-dissection temperature of the cutting element in the range of about 20° C. to about 60° C.

In aspects according to the present disclosure, upon detection of the cutting element contacting tissue, the generator is ramped up to a dissection temperature of about 550° C. In other aspects according to the present disclosure, the generator is configured to regulate the power to maintain the cutting element at the dissection temperature of about 550° C. during open dissection.

In aspects according to the present disclosure, the generator is configured to terminate power to the cutting element upon release of the second switch to allow the cutting element to cool back to the pre-dissection temperature in the range of about 20° C. to about 60° C. before providing power to the cutting element upon re-activation of the second switch.

In aspects according to the present disclosure, power to the cutting element is only provided when the jaw members are disposed in the spaced-apart position and the second switch is activated.

Provided in accordance with other aspects of the present disclosure is an electrosurgical system that includes first and second jaw members each defining a tissue treating surface. The first and second jaw members are pivotably coupled to one another such that either of the first or second jaw members is movable relative to the other from a spaced-apart position to an approximated position to grasp tissue between the tissue treating surfaces. The tissue treating surfaces are adapted to connect to a source of energy to treat tissue grasped therebetween. One of the first or second jaw members includes a thermal cutting element extending from the tissue treating surface thereof.

A generator electrically is coupled to the first and second jaw members and is configured to provide electrical energy thereto to produce a tissue seal between the jaw members upon activation of a first switch and is configured to openly dissect tissue with the thermal cutting element upon activation of a second switch. The generator, upon continued activation of the second switch, is configured to: provide minimal power to the cutting element to maintain a pre-dissection temperature of the cutting element; sense a change in power to maintain the cutting element resistance or change in resistance of the cutting element reflective of tissue contact with the cutting element and ramp up power until the cutting element reaches a dissection temperature; regulate power to maintain the temperature of the cutting element at the dissection temperature during open dissection; reduce power to the cutting element upon release of the second switch to allow the cutting element to cool; and monitor the resistance of the cutting element looking for a change in power to maintain the cutting element resistance or change in resistance of the cutting element reflective of tissue contact with the cutting element and, upon re-activation of second switch, ramp up power until the cutting element reaches the dissection temperature.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

DETAILED DESCRIPTION

Figure 1:
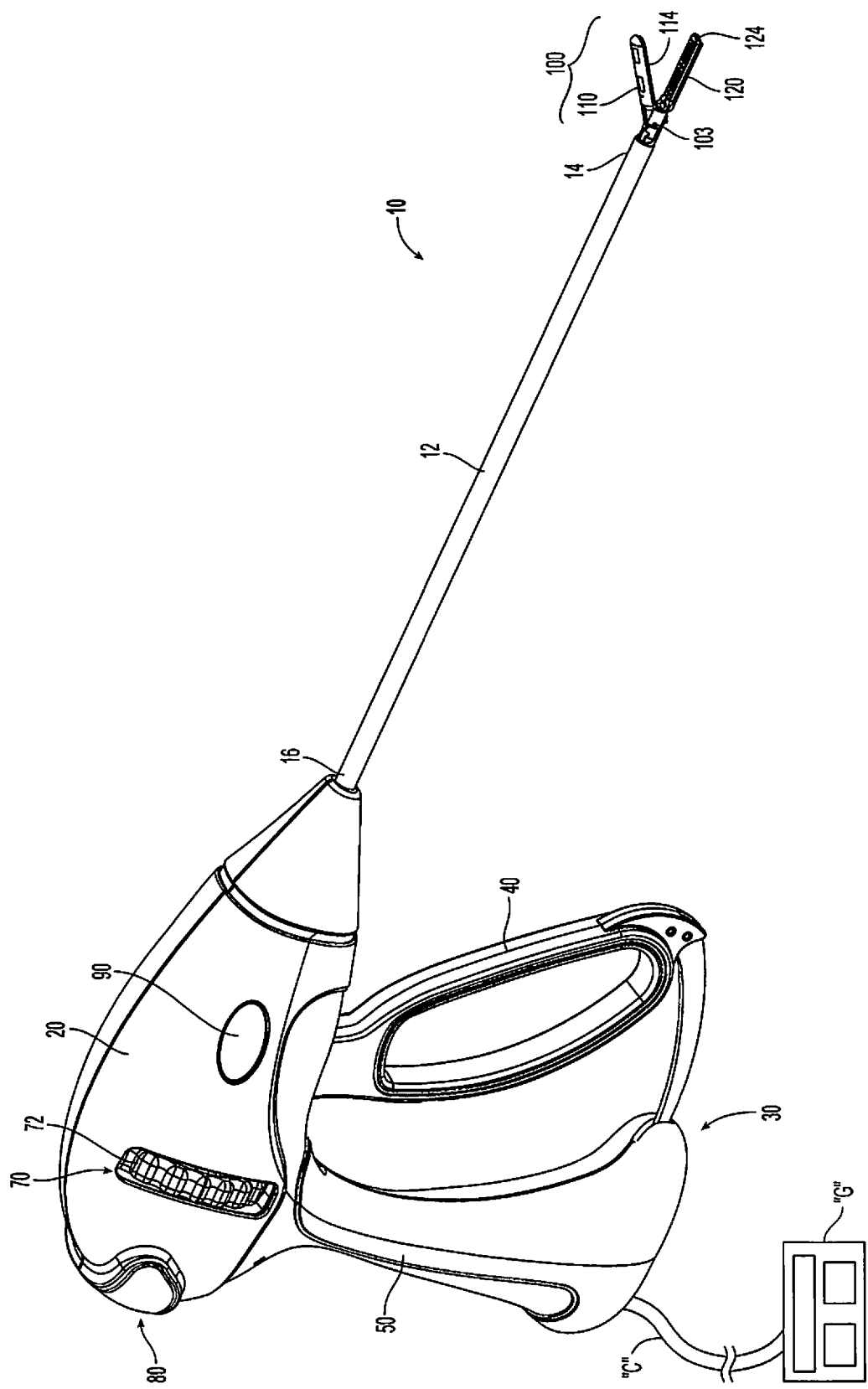
FIG. 1 is a perspective view of a shaft-based electrosurgical forceps provided in accordance with the present disclosure shown connected to an electrosurgical generator.

Referring to FIG. 1, a shaft-based electrosurgical forceps provided in accordance with the present disclosure is shown generally identified by reference numeral 10. Aspects and features of forceps 10 not germane to the understanding of the present disclosure are omitted to avoid obscuring the aspects and features of the present disclosure in unnecessary detail.

Forceps 10 includes a housing 20, a handle assembly 30, a rotating assembly 70, a first activation switch 80, a second activation switch 90, and an end effector assembly 100. Forceps 10 further includes a shaft 12 having a distal end portion 14 configured to (directly or indirectly) engage end effector assembly 100 and a proximal end portion 16 that (directly or indirectly) engages housing 20. Forceps 10 also includes cable "C" that connects forceps 10 to an energy source, e.g., an electrosurgical generator "G." Cable "C" includes a wire (or wires) (not shown) extending therethrough that has sufficient length to extend through shaft 12 in order to connect to one or both tissue treating surfaces 114, 124 of jaw members 110, 120, respectively, of end effector assembly 100 to provide energy thereto. First activation switch 80 is coupled to tissue treating surfaces 114, 124 and the electrosurgical generator "G" for enabling the selective activation of the supply of energy to jaw members 110, 120 for treating, e.g., cauterizing, coagulating/desiccating, and/or sealing, tissue. Second activation switch 90 is coupled to thermal cutting element 130 of jaw member 120 (FIG. 4) and the electrosurgical generator "G" for enabling the selective activation of the supply of energy to thermal cutting element 130 for thermally cutting tissue.

Handle assembly 30 of forceps 10 includes a fixed handle 50 and a movable handle 40. Fixed handle 50 is integrally associated with housing 20 and handle 40 is movable relative to fixed handle 50. Movable handle 40 of handle assembly 30 is operably coupled to a drive assembly (not shown) that, together, mechanically cooperate to impart movement of one or both of jaw members 110, 120 of end effector assembly 100 about a pivot 103 between a spaced apart position and an approximated position to grasp tissue between tissue treating surfaces 114, 124 of jaw members 110, 120. As shown in FIG. 1, movable handle 40 is initially spaced apart from fixed handle 50 and, correspondingly, jaw members 110, 120 of end effector assembly 100 are disposed in the spaced apart position. Movable handle 40 is depressible from this initial position towards fixed handle 50 to a depressed position corresponding to the approximated position of jaw members 110, 120. Rotating assembly 70 includes a rotation wheel 72 that is selectively rotatable in either direction to correspondingly rotate shaft 12 and end effector assembly 100 relative to housing 20.

Figure 2:
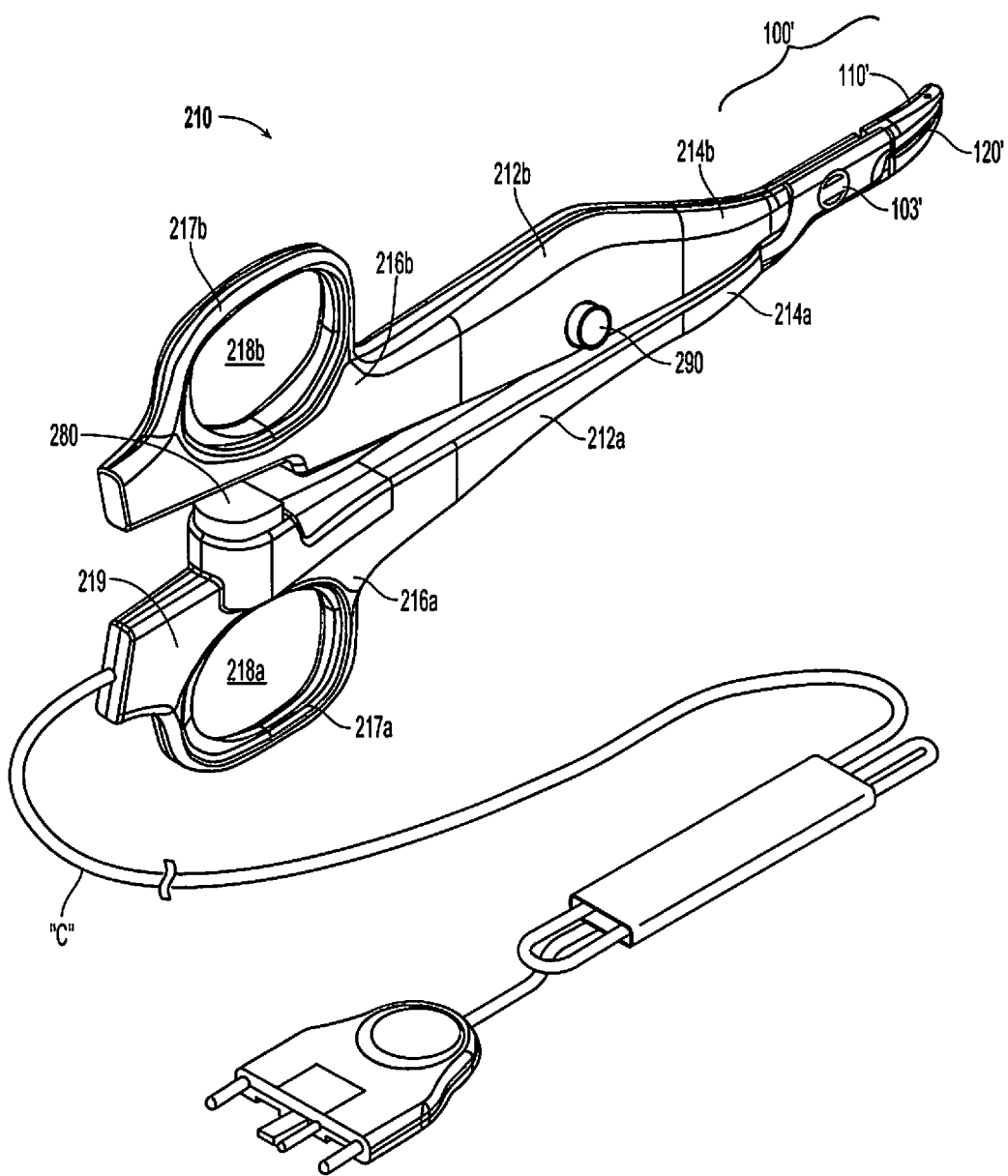
FIG. 2 is a perspective view of a hemostat-style electrosurgical forceps provided in accordance with the present disclosure.

Referring to FIG. 2, a hemostat-style electrosurgical forceps provided in accordance with the present disclosure is shown generally identified by reference numeral 210. Aspects and features of forceps 210 not germane to the understanding of the present disclosure are omitted to avoid obscuring the aspects and features of the present disclosure in unnecessary detail.

Figure 4:
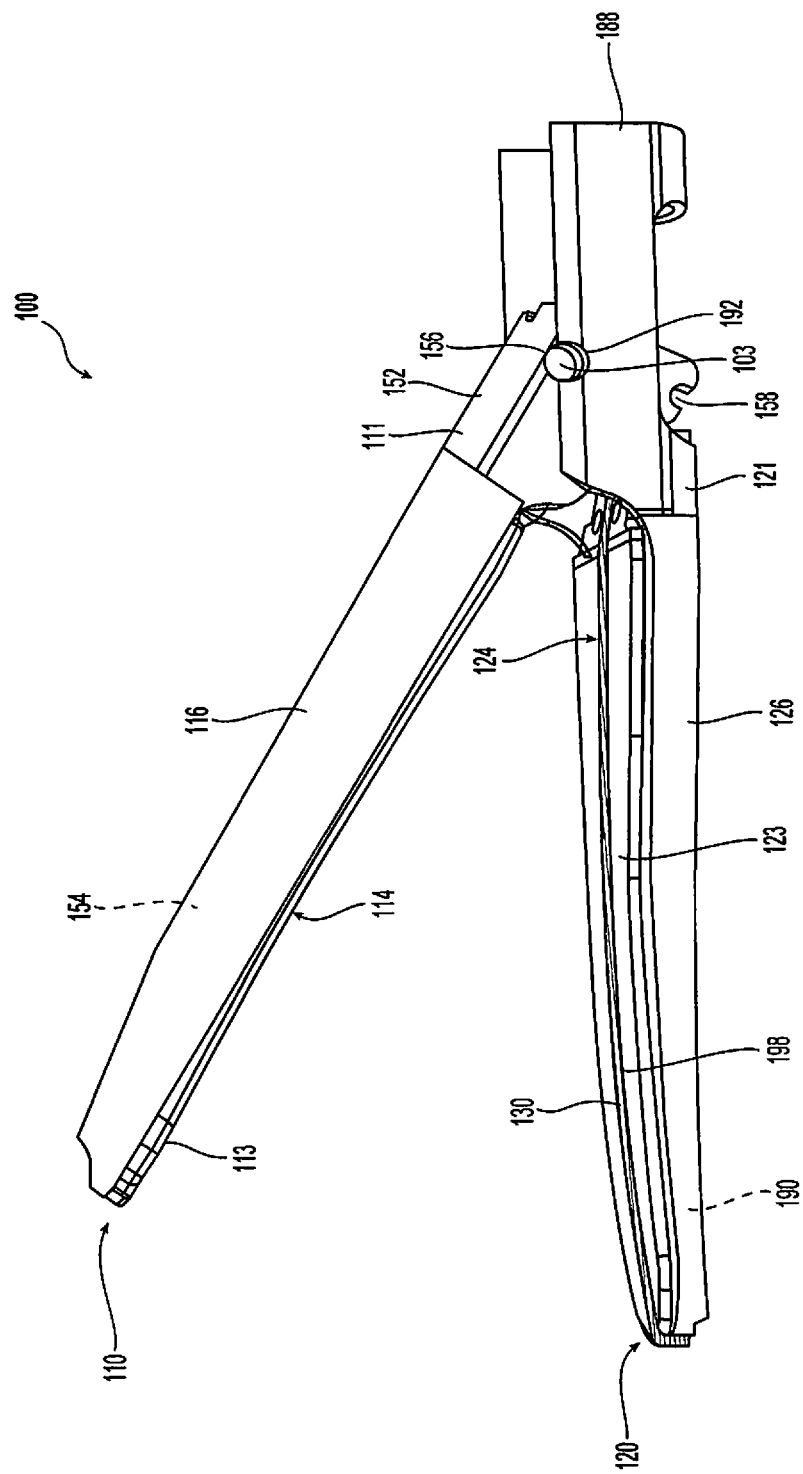
FIG. 4 is a perspective view of an end effector assembly of the forceps of FIG. 1 including first and second jaw members.

Forceps 210 includes two elongated shaft members 212a, 212b, each having a proximal end portion 216a, 216b, and a distal end portion 214a, 214b, respectively. Forceps 210 is configured for use with an end effector assembly 100' similar to and including any of the features of end effector assembly 100 (FIGS. 1 and 4). More specifically, end effector assembly 100' includes first and second jaw members 110', 120' attached to respective distal end portions 214a, 214b of shaft members 212a, 212b. Jaw members 110', 120' are pivotably connected about a pivot 103'. Each shaft member 212a, 212b includes a handle 217a, 217b disposed at the proximal end portion 216a, 216b thereof. Each handle 217a, 217b defines a finger hole 218a, 218b therethrough for receiving a finger of the user. As can be appreciated, finger holes 218a, 218b facilitate movement of the shaft members 212a, 212b relative to one another to, in turn, pivot jaw members 110', 120' from the spaced apart position, wherein jaw members 110', 120' are disposed in spaced relation relative to one another, to the approximated position, wherein jaw members 110', 120' cooperate to grasp tissue therebetween.

One of the shaft members 212a, 212b of forceps 210, e.g., shaft member 212a, includes a proximal shaft connector 219 configured to connect forceps 210 to a source of energy, e.g., electrosurgical generator "G" (FIG. 1). Proximal shaft connector 219 secures a cable "C" to forceps 210 such that the user may selectively supply energy to jaw members 110', 120' for treating tissue. More specifically, a first activation switch 280 is provided on one of the shaft members, e.g., shaft member 212a, for supplying energy to jaw members 110', 120' to treat tissue upon sufficient approximation of shaft members 212a, 212b, e.g., upon activation of first activation switch 280 via the other shaft member 212b. A second activation switch 290 disposed on either or both of shaft members 212a, 212b is coupled to the thermal cutting element (not shown, similar to thermal cutting element 130 of jaw member 120 (FIG. 4)) of one of the jaw members 110', 120' of end effector assembly 100' and to the electrosurgical generator "G" for enabling the selective activation of the supply of energy to the thermal cutting element for thermally cutting tissue.

Jaw members 110', 120' define a curved configuration wherein each jaw member is similarly curved laterally off of a longitudinal axis of end effector assembly 100'. However, other suitable curved configurations including curvature towards one of the jaw members 110', 120' (and thus away from the other), multiple curves with the same plane, and/or multiple curves within different planes are also contemplated. Jaw members 110, 120 of end effector assembly 100 (FIG. 1) may likewise be curved according to any of the configurations noted above or in any other suitable manner.

Figure 3:
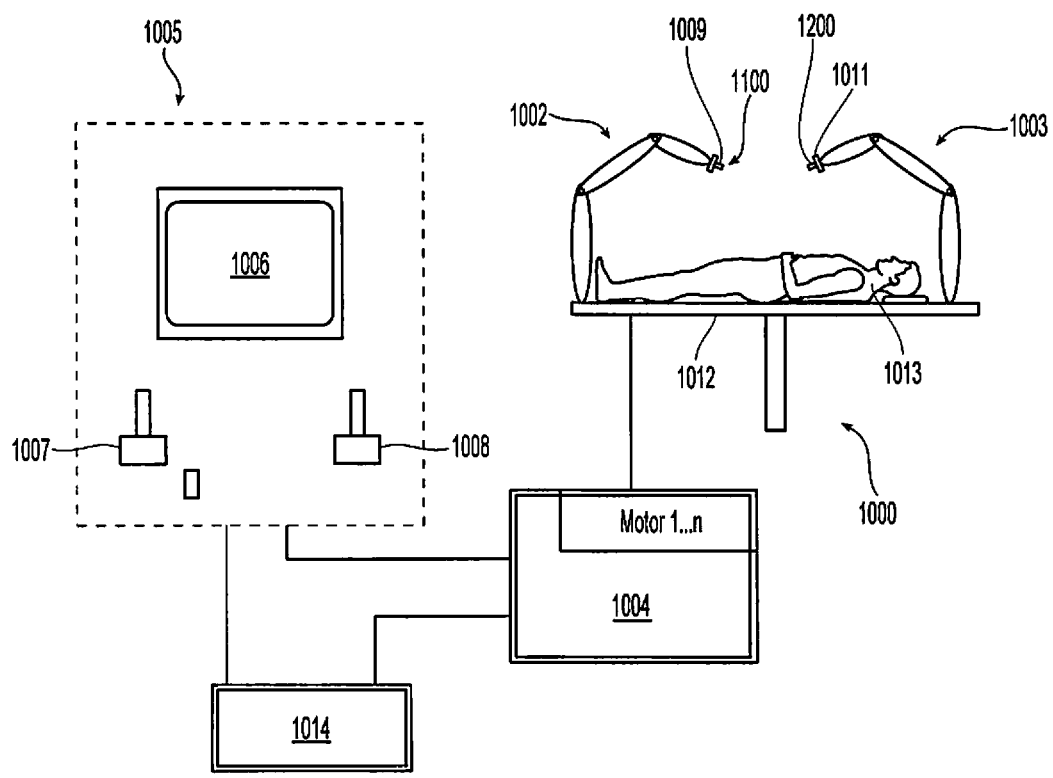
FIG. 3 is a schematic illustration of a robotic surgical instrument provided in accordance with the present disclosure.

Referring to FIG. 3, a robotic surgical instrument provided in accordance with the present disclosure is shown generally identified by reference numeral 1000. Aspects and features of robotic surgical instrument 1000 not germane to the understanding of the present disclosure are omitted to avoid obscuring the aspects and features of the present disclosure in unnecessary detail.

Robotic surgical instrument 1000 includes a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a surgeon may be able to telemanipulate robot arms 1002, 1003 in an operating mode. Robotic surgical instrument 1000 may be configured for use on a patient 1013 lying on a patient table 1012 to be treated in a minimally invasive manner. Robotic surgical instrument 1000 may further include or be capable of accessing a database 1014, in particular coupled to control device 1004, in which are stored, for example, pre-operative data from patient 1013 and/or anatomical atlases.

Each of the robot arms 1002, 1003 may include a plurality of members, which are connected through joints, and an attaching device 1009, 1011, to which may be attached, for example, an end effector assembly 1100, 1200, respectively. End effector assembly 1100 is similar to and may include any of the features of end effector assembly 100 (FIGS. 1 and 4), although other suitable end effector assemblies for coupling to attaching device 1009 are also contemplated. End effector assembly 1200 may be any end effector assembly, e.g., an endoscopic camera, other surgical tool, etc. Robot arms 1002, 1003 and end effector assemblies 1100, 1200 may be driven by electric drives, e.g., motors, that are connected to control device 1004. Control device 1004 (e.g., a computer) may be configured to activate the motors, in particular by means of a computer program, in such a way that robot arms 1002, 1003, their attaching devices 1009, 1011, and end effector assemblies 1100, 1200 execute a desired movement and/or function according to a corresponding input from manual input devices 1007, 1008, respectively. Control device 1004 may also be configured in such a way that it regulates the movement of robot arms 1002, 1003 and/or of the motors.

Turning to FIG. 4, end effector assembly 100, as noted above, includes first and second jaw members 110, 120. Either or both jaw members 110, 120 may include a structural frame 111, 121, an insulative spacer (not shown), a tissue treating plate 113, 123 defining the respective tissue treating surface 114, 124 thereof, and, in aspects, an outer insulative jacket 116, 126. Tissue treating plates 113, 123 may be pre-formed and engaged with the insulative spacers and/or other portion(s) of jaw members 110, 120 via, for example, overmolding, adhesion, mechanical engagement, etc., or may be deposited onto the insulative spacers, e.g., via sputtering or other suitable deposition technique.

Jaw member 110, as noted above, includes a structural frame 111, an insulative spacer (not shown), a tissue treating plate 113 defining tissue treating surface 114, and, in aspects, an outer insulative jacket 116. Structural frame 111 may be formed from stainless steel or other suitable material configured to provide structural support to jaw member 110. Structural frame 111 includes a proximal flange portion 152 about which jaw member 110 is pivotably coupled to jaw member 120 via pivot 103 and a distal body portion 154 that supports the other components of jaw member 110, e.g., the insulative spacer, tissue treating plate 113, and outer insulative jacket 116 (where provided). In shaft-based or robotic configurations, proximal flange portion 152 enables operable coupling of jaw member 110 to the drive assembly (not shown) to enable pivoting of jaw member 110 relative to jaw member 120 in response to actuation of the drive assembly. More specifically, proximal flange portion 152 may define an aperture 156 for receipt of pivot 103 and at least one catch 158 for receipt of a drive pin of the drive assembly (not shown) such that translation of the drive pin, e.g., in response to actuation of movable handle 40 (FIG. 1) or a robotic drive, pivots jaw member 110 about pivot 103 and relative to jaw member 120 between the spaced apart position and the approximated position. However, other suitable drive arrangements are also contemplated, e.g., using cam pins and cam slots, a screw-drive mechanism, etc. In hemostat-style devices, proximal flange portion 152 is secured to one of the shaft members, e.g., shaft member 212a of forceps 210 (see FIG. 2). Proximal flange portion 152 may be bifurcated to define a pair of spaced apart proximal flange portion segments or may otherwise be configured.

Distal body portion 154 of structural frame 111 extends distally from proximal flange portion 152 to support the other components of jaw member 110. The insulative spacer of jaw member 110 is supported on distal body portion 154 of structural frame 111 and is formed from an electrically insulative material capable of withstanding high temperatures such as, for example, up to at least 400° C., although other configurations are also contemplated. The insulative spacer may be formed from ceramic or other suitable material, e.g., PTFE, PEEK, PEI, etc. Tissue treating plate 113 is supported or received on the insulative spacer and is electrically connected, e.g., via one or more electrical leads (not shown), to first activation switch 80 (FIG. 1) and electrosurgical generator "G" (FIG. 1) to enable selective energization of tissue treating plate 113, e.g., as one pole of a bipolar Radio Frequency (RF) electrosurgical circuit. However, other suitable energy modalities, e.g., thermal, ultrasonic, light, microwave, infrared, etc., are also contemplated. The insulative spacer serves to electrically isolate structural frame 111 and tissue treating plate 113 from one another.

Continuing with reference to FIG. 4, jaw member 120 includes a structural frame 121, an insulative spacer (not shown), a tissue treating plate 123 defining tissue treating surface 124, and, in aspects, an outer insulative jacket 126. Jaw member 120 further include thermal cutting element 130. Structural frame 121 of jaw member 120 defines a proximal flange portion 188 and a distal body portion 190 extending distally from proximal flange portion 188. Proximal flange portion 188 may be bifurcated to define a pair of spaced apart proximal flange portion segments or may define any other suitable configuration. Proximal flange portion 188 of jaw member 120 and proximal flange portion 152 of jaw member 110 may define a nestled configuration, e.g., wherein one of the proximal flange portions 152, 188 is received within the other, an overlapping configuration, e.g., wherein proximal flange portions 152, 188 at least partially overlap one another, or an offset configuration, e.g., wherein proximal flange portions 152, 188 are positioned in side-by-side relation. Regardless of the particular arrangement of proximal flange portions 152, 188, proximal flange portion 188 further defines a cut out 192 configured for receipt of pivot 103, e.g., welded or otherwise secured therein, to pivotably couple jaw members 110, 120 with one another. Proximal flange portion 188 may be secured to shaft 12 (FIG. 1) in shaft-based configurations (or a corresponding shaft portion in robotic configurations); alternatively, a bilateral configuration may be provided whereby both jaw member 110 and jaw member 120 are pivotable relative to shaft 12 (FIG. 1). In hemostat-style configurations, proximal flange portion 188 may be secured to elongated shaft 212b (FIG. 2).

The insulative spacer of jaw member 120 is supported on distal body portion 190 of structural frame 121 and is formed from an electrically insulative material capable of withstanding high temperatures such as, for example, up to at least 400° C., although other configurations are also contemplated. The insulative spacer may be formed from ceramic or other suitable material, e.g., PTFE, PEEK, PEI. Tissue treating plate 123 is supported or received on the insulative spacer. Tissue treating plate 123, in particular, defines a longitudinally extending slot 198 therethrough along at least a portion of the length thereof. Slot 198 may be transversely centered on tissue treating surface 124 or may be offset relative thereto and may be linear, curved, include angled sections, etc. similarly or differently from the configuration, e.g., curvature, of jaw member 120. Slot 198 exposes a portion of thermal cutting element 130, which may be recessed relative to tissue treating surface 124, substantially co-planar with tissue treating surface 124, or protrude beyond tissue treating surface 124 towards jaw member 110. In aspects where thermal cutting element 130 protrudes, thermal cutting element 130 may contact an opposing portion of jaw member 110 to set a minimum gap distance, e.g., of from about 0.001 inches to about 0.006 inches, between tissue treating surfaces 114, 124 in the approximated position of jaw members 110, 120.

Tissue treating plate 123 is electrically connected, e.g., via one or more electrical leads (not shown), to first activation switch 80 (FIG. 1) and electrosurgical generator "G" (FIG. 1) to enable selective energization of tissue treating plate 123, e.g., as the other pole of the bipolar (RF) electrosurgical circuit including tissue treating plate 113. In this manner, in the approximated position of jaw members 110, 120 grasping tissue therebetween, bipolar RF electrosurgical energy may be conducted between tissue treating plates 113, 123 and through the grasped tissue to treat, e.g., seal, the grasped tissue. However, other suitable energy modalities, e.g., thermal, ultrasonic, light, microwave, infrared, etc., are also contemplated, as are other suitable tissue treatments, e.g., coagulation.

Thermal cutting element 130 may be secured within and directly to the insulative spacer 122 of jaw member 120 in any suitable manner, e.g., adhesive, friction fitting, overmolding, mechanical engagement, etc., or may be indirectly secured relative to the insulative spacer (in contact with or spaced apart therefrom) via attachment to one or more other components of jaw member 120. Alternatively, the insulative spacer may be omitted and thermal cutting element 130 secured within jaw member 120 (to one or more components thereof) in any other suitable manner. Other suitable configurations for supporting thermal cutting element 130 within jaw member 120 are also contemplated. Thermal cutting element 130 may protrude distally beyond the distal tip of the insulative spacer of jaw member 120 (thus defining the distal-most extent of jaw member 120), may be substantially flush therewith, or may be recessed relative thereto. In aspects where end effector assembly 100, or a portion thereof, is curved, thermal cutting element 130 may similarly be curved.

Figure 5:
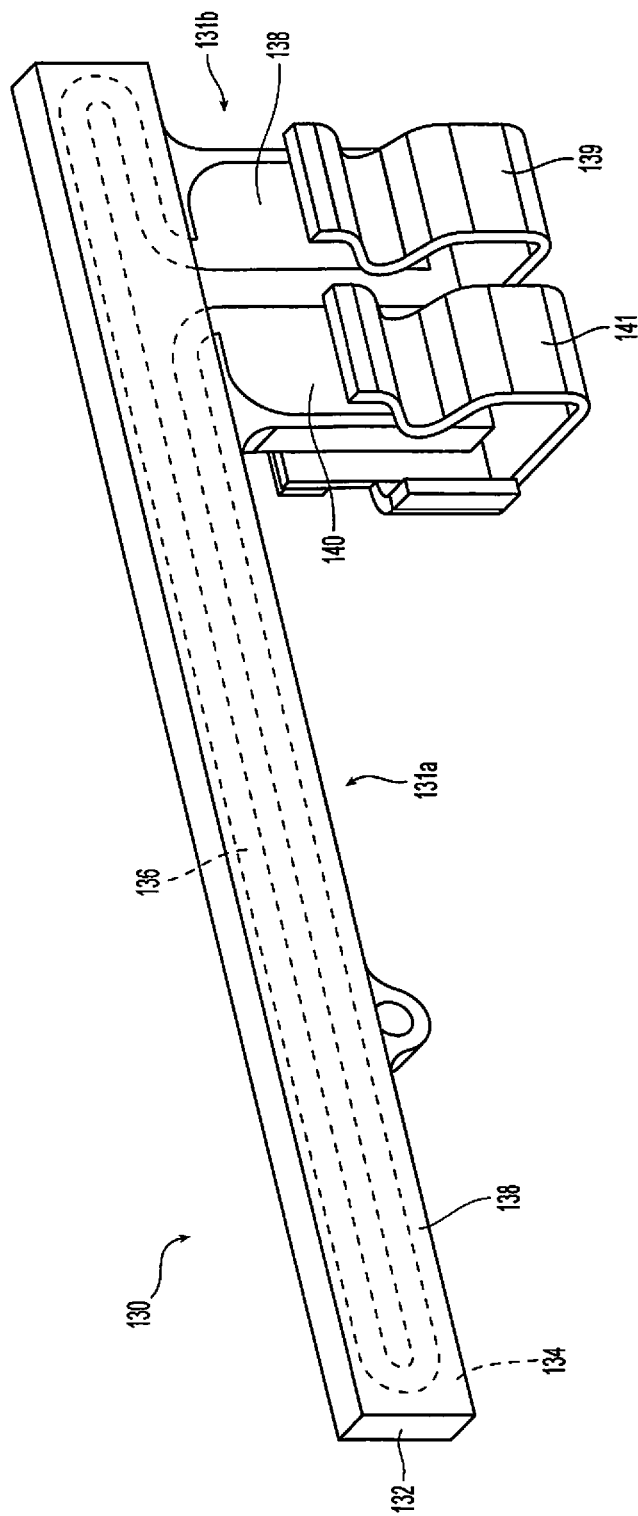
FIG. 5 is a perspective view of the thermal cutting element of the second jaw member of the end effector assembly of FIG. 4.

With additional reference to FIG. 5, thermal cutting element 130 includes a body 131*a* and a proximal extension 131*b*. Thermal cutting element 130 is formed from a base substrate 132 and includes an insulating layer 134 disposed on at least one side of base substrate 132, and a conductive heater trace 136 disposed on insulating layer 134 on at least one side of base substrate 132. Conductive heater trace 136 extends distally along body 131*a* of thermal cutting element 130 and loops back proximally such that first and second ends 138, 140 of conductive heater trace 136 are disposed at proximal extension 131*b* of thermal cutting element 130. First and second contact clips 139, 141 (or other suitable electrical connections) are coupled to proximal extension 131*b* of thermal cutting element 130 in electrical communication with first and second ends 138, 140, respectively, of conductive heater trace 136 for connecting lead wires (not shown) to thermal cutting element 130 to enable application of an AC voltage thereto to heat thermal cutting element 130, e.g., via resistive heating. More specifically, the lead wires electrically connect thermal cutting element 130 to second activation switch 90 (FIG. 1) and electrosurgical generator "G" (FIG. 1) to enable selective activation of the supply of an AC voltage to thermal cutting element 130 for heating thermal cutting element 130 to heat and thereby thermally cut tissue. Thermal cutting element 130 may be configured to cut previously (or concurrently) sealed tissue grasped between jaw members 110, 120, tissue extending across jaw member 120, tissue adjacent the distal end of jaw member 120, etc. In addition to or as an alternative to cutting, thermal cutting element 130 may be configured for other tissue treatment, e.g., coagulation.

Base substrate 132 may be formed from any suitable material such as, for example, stainless steel, aluminum, aluminum alloys, titanium, titanium alloys, other suitable materials, combinations thereof, etc. Base substrate 132 may be formed via laser cutting, machining, casting, forging, fine-blanking, or any other suitable method. Base substrate 132 may define a thickness of, in aspects, from about 0.003 in to about 0.030 in; in other aspects, from about 0.004 in to about 0.015 in; and in still other aspects, from about 0.005 in to about 0.012 in.

Insulating layer 134, as noted above, may be disposed on either or both sides of base substrate 132. Insulating layer 134 may be a Plasma Electrolytic Oxidation (PEO) coating formed via PEO of either or both sides of base substrate 132. Other suitable materials for insulating layer 134, e.g., PTFE, PEEK, PEI, glass, etc., and/or methods of forming insulating layer 134, e.g., anodization, deposition, spraying, adhesion, mechanical attachment, etc., on either or both sides of base substrate 132 are also contemplated. Where insulating layer 134 is disposed on both sides of base substrate 132, the sides may be of the same or different materials and/or of the same or different thicknesses. Insulating layer 134 may define a thickness (on either or both sides of base substrate 132), in aspects, from about 0.0005 in to about 0.0015 in; in other aspects, from about 0.0007 in to about 0.0013 in; and in still other aspects, from about 0.0009 in to about 0.0012 in. In aspects wherein an insulating base substrate 132, e.g., ceramic, is utilized, insulating layer 134 may be omitted. Further, in aspects, multiple insulating layers 134 are provided on the same side, e.g., two insulating layers 134 on top of one another, each of which may define a thickness (similar or different from one another) within the above-noted ranges or which may collectively define a thickness within the above-noted ranges.

Conductive heater trace 136, as noted above, is disposed on insulating layer 134 (or directly on base substrate 132 where base substrate 132 itself is insulating) on one side of thermal cutting element 130, although it is also contemplated that conductive heater trace 136 extend to the other side of thermal cutting element 130 or that a second conductive heater trace 136 be provided on the other side of thermal cutting element 130. Conductive heater trace 136 may be formed from, for example, platinum, nichrome, kanthal, combinations thereof, or other suitable metal(s) and is disposed on insulating layer 134 via a deposition process, e.g., sputtering, via screen printing, via sintering, or in any other suitable manner. Conductive heater trace 136 may define a thickness, in aspects, from about 0.0002 in to about 0.0030 in; in other aspects, from about 0.0006 in to about 0.002 in; and in still other aspects, from about 0.0008 in to about 0.0012 in.

In aspects, thermal cutting element 130 further includes an encapsulating layer 138 disposed on either or both sides of body 131*a* of thermal cutting element 130 and/or proximal extension 131*b* of thermal cutting element 130. For example, encapsulating layer 138 may encapsulate body 131*a* of thermal cutting element 130 on the side of thermal cutting element 130 including an insulating layer 134 and conductive heater trace 136, although other configurations are also contemplated. Encapsulating layer 138 may define a thickness (on either or both sides of base substrate 132), in aspects, from about 0.0005 in to about 0.0015 in; in other aspects, from about 0.0007 in to about 0.0013 in; and in still other aspects, from about 0.0009 in to about 0.0012 in.

Thermal cutting element 130 as a whole (e.g., including base substrate 132, one or more insulating layers 134 on either or both sides, conductive heater trace 136, and, encapsulating layer 138 on either or both sides) may define a thickness, in aspects, from about 0.010 in to about 0.018 in; in other aspects, from about 0.011 to about 0.016 in; and in still other aspects, from about 0.013 in to about 0.015 in.

Referring still to FIGS. 4 and 5, thermal cutting element 130 may be configured to receive an applied voltage ($V_{AC}$), e.g., the voltage output from electrosurgical generator "G" (FIG. 1) to thermal cutting element 130, in aspects, from about 5 volts to about 250 volts; in other aspects, from about 10 volts to about 175 volts; and in still other aspects, from about 25 volts to about 100 volts.

Thermal cutting element 130 may be configured to operate in one or more different modes, e.g., controllable/settable at electrosurgical generator "G" (FIG. 1) or on housing 20

(FIG. 1) such as, for example, adjacent to or incorporated with second activation switch 90 (FIG. 1). More specifically, thermal cutting element 130 may have a single operating mode and corresponding operating temperature for all functions, or may have multiple operating modes each having a corresponding operating temperature for one or more functions such as, for example: back scoring, tenting, plunger cutting, jaws open cutting, jaws closed cutting, slow cutting, fast cutting, spot coagulation, etc. The operating temperatures for the one or more operating modes may be similar or different and any or all may be, in aspects, of at least about 350° C.; in other aspects, from about 350° C. to about 550° C.; in yet other aspects, about or at least 550° C.; in still yet other aspects, from about 400° C. to about 500° C.; and in other aspects, from about 425° C. to about 475° C.

A difference between the resistance of thermal cutting element 130 at room temperature, e.g., 20° C., and an operating temperature, e.g., 550° C., may be, in aspects, from about 5 ohms to about 1500 ohms; in other aspects, from about 10 ohms to about 1000 ohms; and in still other aspects, from about 20 ohms to about 400 ohms.

A Temperature Coefficient of Resistance (TCR) of thermal cutting element 130 may be, in aspects, at least 50 ppm/° C.; in other aspects, at least 900 ppm/° C.; and in still other aspects, at least 3000 ppm/° C.

The power (W) output, e.g., from electrosurgical generator "G" (FIG. 1), to thermal cutting element 130 at the operating temperature of thermal cutting element 130, e.g., 550° C., may be, in aspects, at most 50 W; in other aspects, at most 40 W; and in still other aspects, at most 32 W. The initial power (W) output, e.g., from electrosurgical generator "G" (FIG. 1), to thermal cutting element 130 to reach the operating temperature may be, in aspects, at most 100 W; in other aspects, at most 75 W; and in still other aspects, at most 50 W.

Various different values and ranges for the configuration and operating parameters of thermal cutting element 130 are detailed above. The present disclosure also specifically contemplates any and all combinations of these values and/or ranges as well as any and all ratios and/or ratio ranges of the values and/or ranges of two or more of these operating parameters. For example, appropriate materials, thicknesses, and/or operating parameters may be selected such that, in aspects, thermal cutting element 130 defines a configuration that maximizes the difference between the resistance of thermal cutting element 130 at room temperature and at the operating temperature and, at the same time, minimizes the applied voltage ($V_{AC}$), all while enabling thermal cutting element 130 to reach a suitable operating temperature.

As mentioned above, during a typical sealing and cutting process the generator "G" cycles through the various algorithms and modes to effectively seal and divide tissue upon the actuation, respective switches, e.g., switches 80 and 90. In certain circumstances a surgeon may opt to dissection tissue with the forceps, e.g., forceps 10. Since the electrical surfaces of the forceps 10, e.g., tissue treating surfaces 114, 124 of jaw members 110, 120 and the cutting element 130, are disposed between the jaw members 110, 120, the jaw members 110, 120 must be spaced relative to one another to dissect tissue using the cutting element 30. In other words, when the jaw members 110, 120 are closed about tissue, the generator "G" can be activated by switch 80 to seal tissue and cutting element 130 can be activated by switch 90 to cut tissue disposed between the jaw members 110, 120.

When the jaw members 110 and 120 are disposed in an open configuration, it is typically undesirable to allow activation of either the tissue contacting surface 114, 124 or the cutting element 130 and, as a result, in certain circumstances, one or more mechanical or electrical safety mechanisms (not shown) may be put in place to avoid unintended activation. Moreover, having a tissue sealing surface 114, 124 or active cutting element 130 activated at the respective power level to seal or cut tissue prior to tissue contact can have unwanted tissue effects. In particular, having the switch 90 activated and generating high cutting power with the cutting element 130 prior to tissue contact may result in unintended tissue dissection.

FIGS. 6A-10B illustrate several variations of a low power sensing mode for incorporation into one or more of the above-identified surgical forceps 10, 210. When a low power mode is incorporated into the generator algorithm (or otherwise incorporated into the forceps 10, 210), the generator "G" only delivers low power to the cutting element 130 (low power is defined as a power level that does not cause any tissue effect if the cutting element 130 inadvertently contacts tissue) when activated and until tissue is sensed in contact with the cutting element 130. In other words, high cutting power is only delivered to the cutting element 130 if tissue is "sensed" to be in contact with the cutting element 130. If no tissue is "sensed" to be in contact with the cutting element 130, no additional power is delivered (power is not ramped up from a low power level) to the tissue for dissection.

Figure 6A:
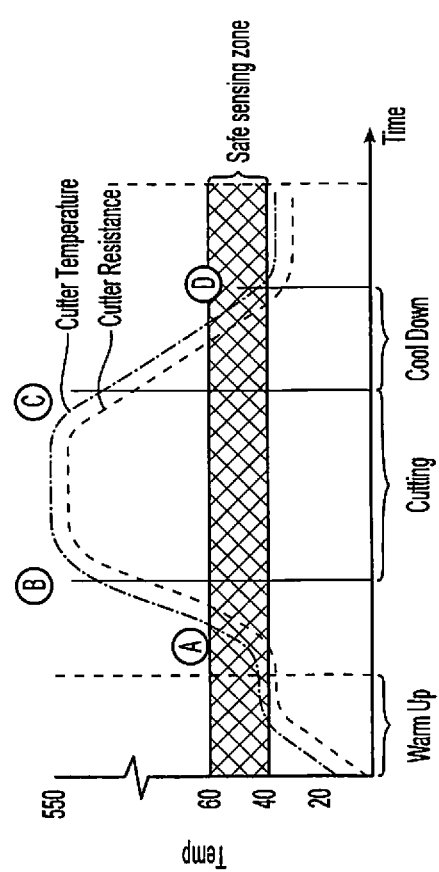
FIG. 6A is an illustrative graph comparing Cutting Element Resistance and Temperature over a cutting period in accordance with the present disclosure.
Figure 6B:
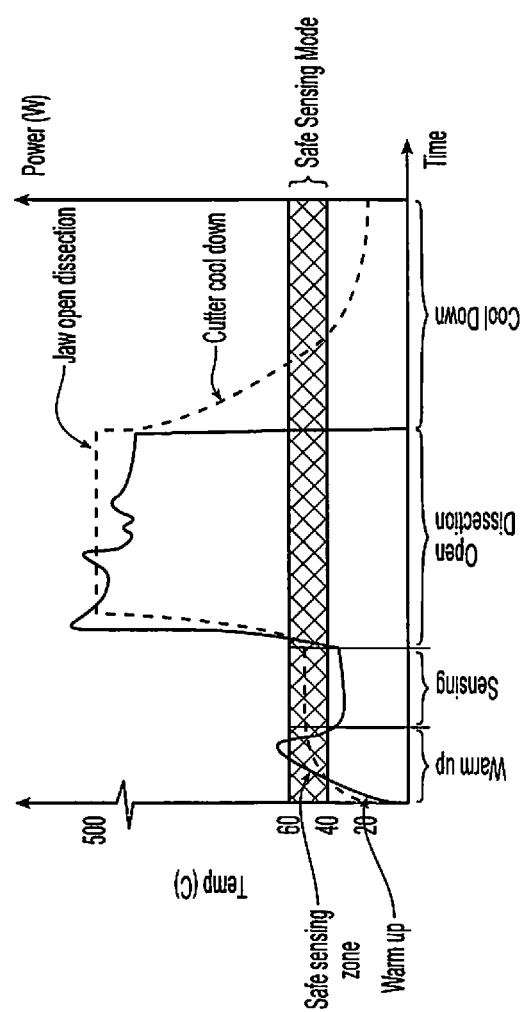
FIG. 6B is an illustrative graph comparing Power and Temperature over a cutting period in accordance with the present disclosure.

FIGS. 6A and 6B are a graphical illustrations of a low power dissection mode cycle showing, respectively, a graph of resistance and temperature of the cutting element 130 over time and power and temperature of the cutting element 130 over time. More particularly, when the switch 90 is activated into the low power mode, the switch queries the jaw members 110, 120 to determine if the jaw members 110, 120 are open or closed. Various electrical and mechanical sensing mechanisms in the generator "G", switch 90 or jaw members 110, 120 may be utilized to makes this determination. If the jaw members 110, 120 are closed, the sealing and cutting cycles may be initiated (as described above). If the jaw members 110, 120 are open, the generator "G" sends low power to the cutting element 130 which both warms up the cutting element 130 and places the cutting element 130 in a so-called "sensing" mode (FIG. 6B). During this time, the temperature and resistance of the cutting element 130 begins to rise. The generator "G" regulates the power to warm up the cutting element 130 (FIG. 6B) and to maintain the temperature of the cutting element 130 within a "safe zone", e.g., between about room temperature (about 20° C.) and a temperature known to initiate a thermal tissue response (about 60° C.).

While in the low power mode and after the warm-up period, the generator "G" continually senses for the initiation of tissue contact with the cutting element 130. As can be appreciated, sensing tissue contact with the cutting element 130 may be accomplished through various known electrical, mechanical or electro-mechanical circuits and/or mechanisms, e.g., impedance, resistance, optics, sensors, etc. Once tissue is sensed to be in contact with the cutting element 130, high cutting power is delivered to the cutting element 130 to dissect tissue. High cutting power is only delivered to the cutting element 130 if tissue is "sensed" to be in contact with the cutting element 130 and various feedback loops or safety circuits may be employed to insure actual tissue contact. If no tissue is "sensed" to be in contact with the cutting element 130, no additional power is delivered (power is not ramped up from a low power level) to the tissue for dissection.

As shown in both FIGS. 6A and 6B, power is ramped up over time which causes the temperature of the cutting element 130 to increase along with the resistance of the cutting element 130 until a desired temperature is reached, e.g., about 550° C., to dissect tissue. The power to the cutting element 130 is then regulated to maintain the temperature of the cutting element 130 within this general temperature range (e.g., about 550° C.) while the switch 90 remains activated. As discussed above, various different values and ranges for the configuration and operating parameters of thermal cutting element 130 are detailed above. The present disclosure also specifically contemplates any and all combinations of these values and/or ranges as well as any and all ratios and/or ratio ranges of the values and/or ranges of two or more of these operating parameters. For example, appropriate materials, thicknesses, and/or operating parameters may be selected such that, in aspects, thermal cutting element 130 defines a configuration that maximizes the difference between the resistance of thermal cutting element 130 at room temperature and at the dissection temperature and, at the same time, minimizes the applied voltage ($V_{AC}$), all while enabling thermal cutting element 130 to reach a suitable dissection temperature. Other optimizations are also contemplated.

Once the switch 90 is deactivated, e.g., power is cut, and both the temperature and resistance of the cutting element 130 dissipate over time (See. FIG. 6A) until the temperature resides within the "safe zone". The power and temperature graph (FIG. 6B) also depicts a similar dissipation of temperature once the power is cut. Re-activation of the switch 90 may occur once the temperature of the cutting element 130 reaches the "safe zone" (and an indicator (visual, tactile, or audible) may be employed for this purpose) or the generator "G" may be programmed to follow on or more of the algorithms shown below with respect to FIGS. 7A-10B.

Figure 7A:
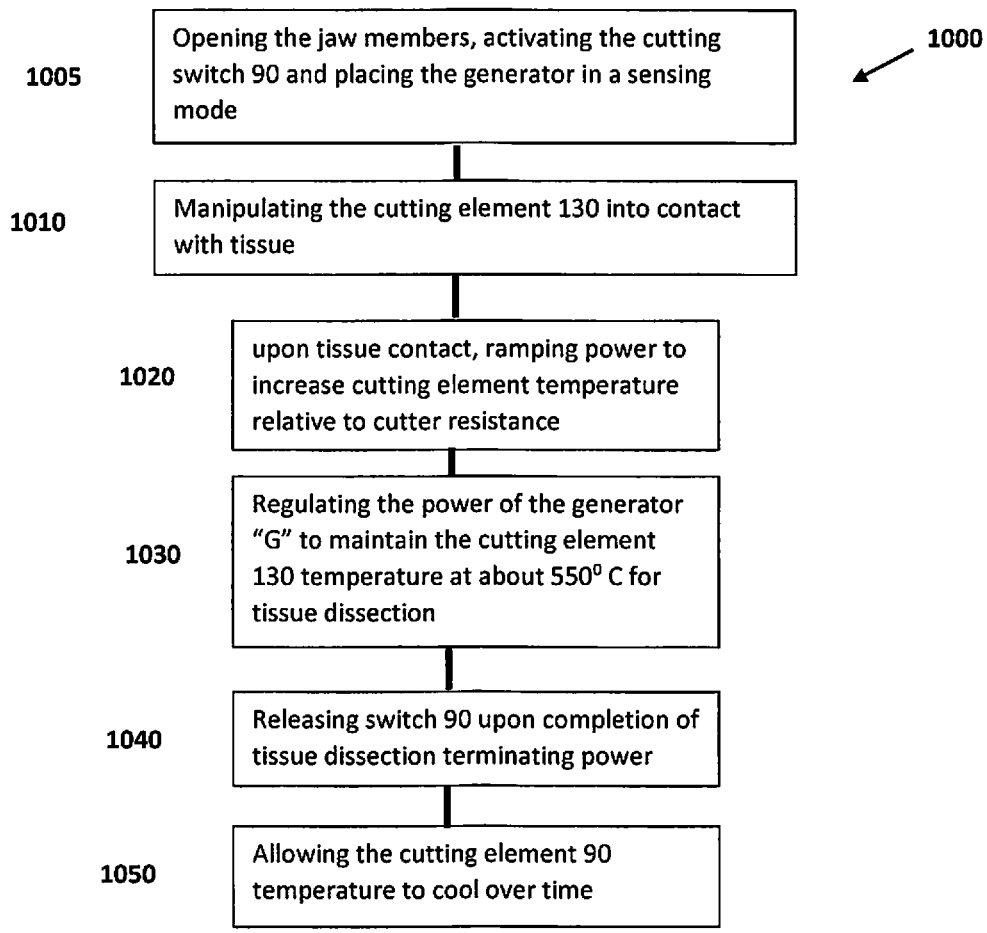
FIG. 7A is a flow chart showing a standard jaw open dissection cycle.
Figure 7B:
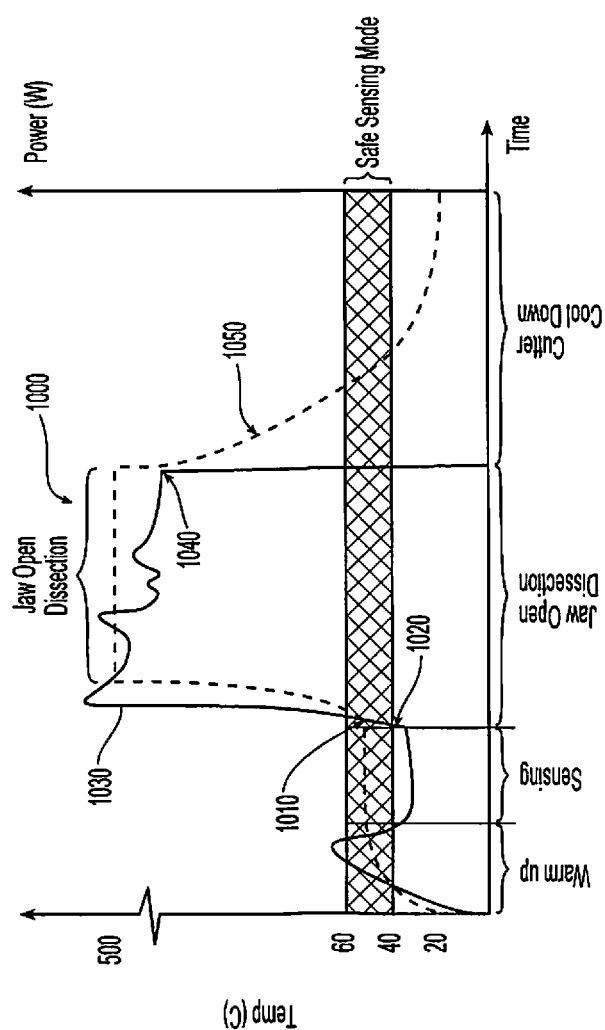
FIG. 7B is an illustrative graph corresponding to the flow chart of FIG. 7A.

FIG. 7A is a flow chart showing the various steps associated with a method 1000 for performing an open dissection cycle of tissue according to the embodiment described with respect to FIGS. 6A and 6B above and FIG. 7B illustrates an accompanying graph of the method highlighting the various steps. As an initial step 1005, the jaw members, e.g., jaw members 110, 120, are opened and the cutting switch 90 is activated and placed in a sensing mode (as discussed above). In step 1010, the cutting element 130 is manipulated into contact with tissue. In step 1020, upon tissue contact, power is ramped to increase the cutting element 130 temperature relative to cutter resistance. In step 1030, the generator "G" regulates power to maintain cutting element 130 temperature at about 550° C. for tissue dissection. In step 1040, switch 90 is released upon completion of tissue dissection and power is terminated. In step 1050, the cutting element 130 temperature cools over time.

Figure 8A:
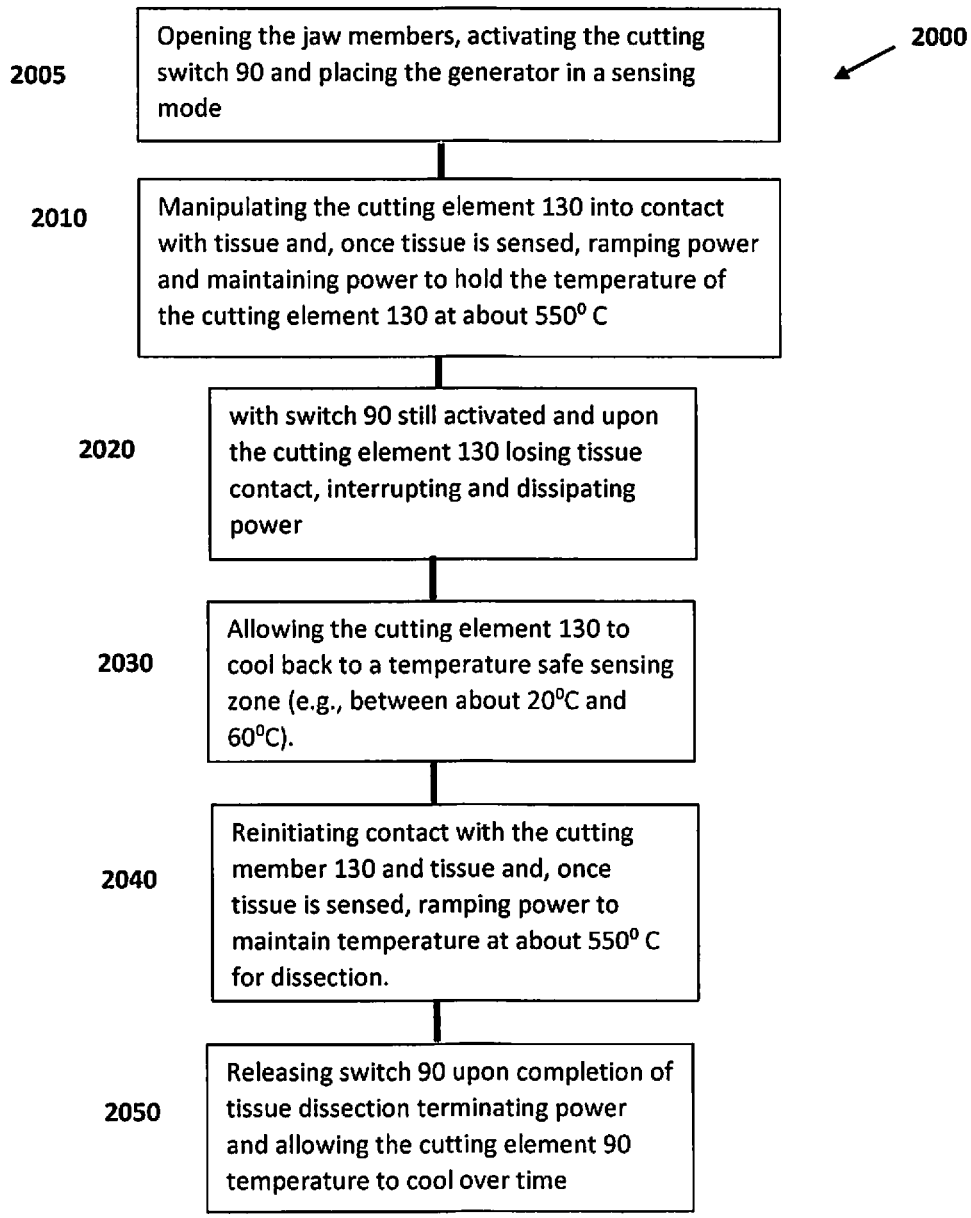
FIG. 8A is a flow chart showing a jaw open dissection cycle with intermittent cutting.
Figure 8B:
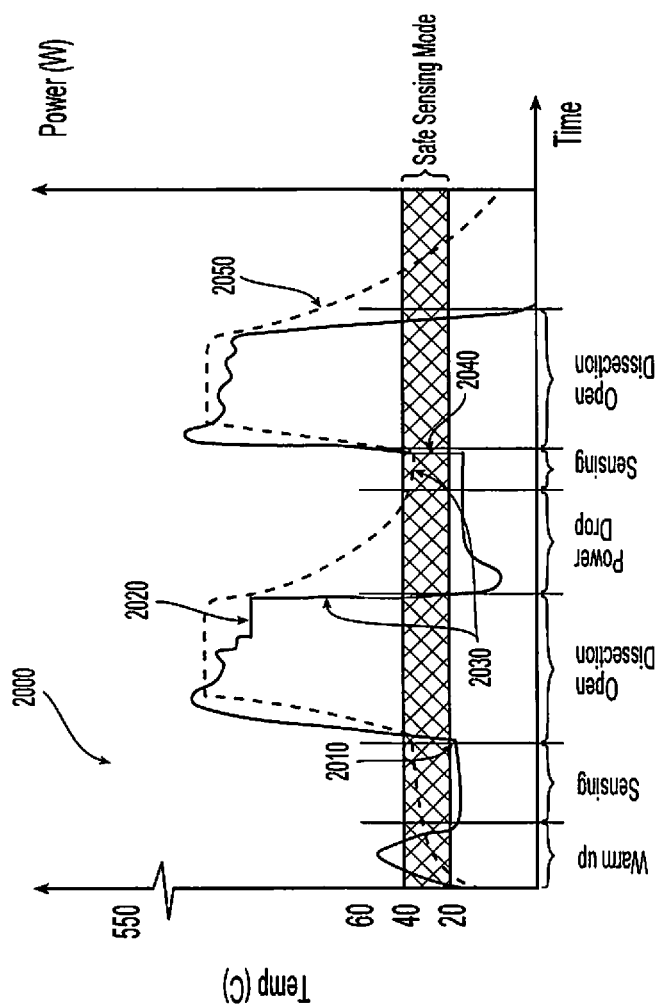
FIG. 8B is an illustrative graph corresponding to the flow chart of FIG. 8A.

FIG. 8A is a flow chart showing the various steps associated with a method 2000 for performing an open dissection cycle of tissue with intermittent cutting according to another embodiment described with respect to FIGS. 6A and 6B above and FIG. 8B illustrates an accompanying graph of this method highlighting the various steps. As an initial step 2005, the jaw members, e.g., jaw members 110, 120, are opened and the cutting switch 90 is activated and placed in a sensing mode (as discussed above). In step 2010, the cutting element 130 is manipulated into contact with tissue and, once tissue is sensed, power is ramped and maintained to hold the temperature of the cutting element 130 at about 550° C. In step 2020, with switch 90 still activated, upon the cutting element 130 losing tissue contact, constant power is identified and turned off allowing the heat to dissipate. In step 2030, the cutting element 130 cools back to the temperature safe sensing zone (e.g., between about 20° C. and 60° C.). In step 2040, the cutting member 190 re-initiates contact with tissue and, once tissue is sensed, power is ramped again to maintain temperature of the cutting element 130 at about 550° C. for dissection. In step 2050, switch 90 is released upon completion of tissue dissection and power is terminated and the cutting element 130 temperature cools over time.

Figure 9A:
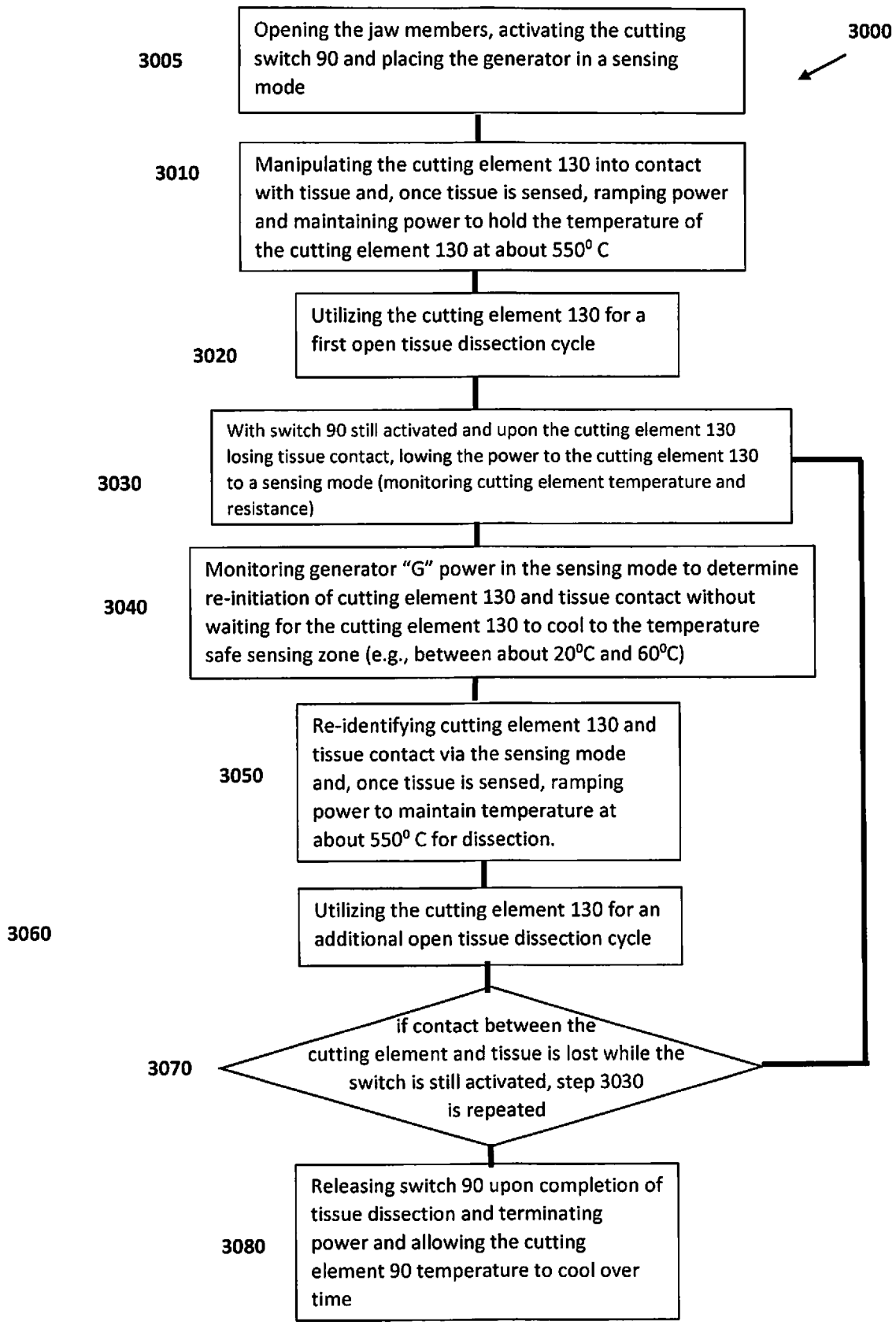
FIG. 9A is a flow chart showing a jaw open dissection cycle with intermittent cutting and short cooling.
Figure 9B:
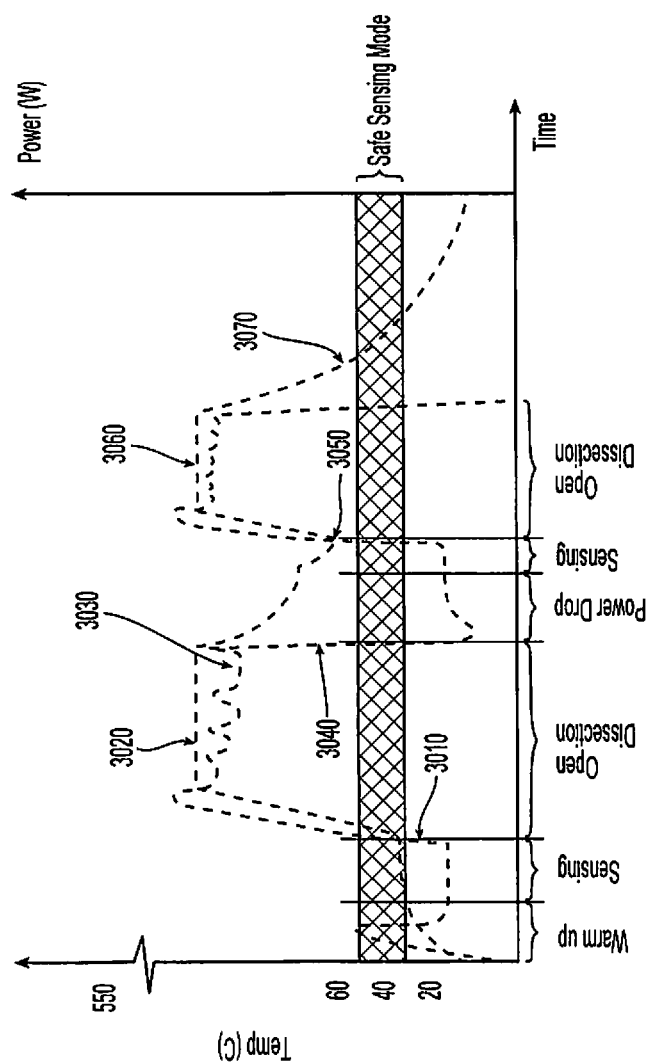
FIG. 9B is an illustrative graph corresponding to the flow chart of FIG. 9A.

FIG. 9A is a flow chart showing the various steps associated with a method 3000 for performing an open dissection cycle of tissue with intermittent cutting with a shortened cooling time according to another embodiment described with respect to FIGS. 6A and 6B above and FIG. 9B illustrates an accompanying graph of this method highlighting the various steps. As an initial step 3005, the jaw members, e.g., jaw members 110, 120, are opened and the cutting switch 90 is activated and placed in a sensing mode (as discussed above). In step 3010, the cutting element 130 is manipulated into contact with tissue and, once tissue is sensed, power is ramped and maintained to hold the temperature of the cutting element 130 at about 550° C. In step 3020, the cutting element 130 is utilized for a first open tissue dissection cycle. In step 3030, with switch 90 still activated, upon the cutting element 130 losing tissue contact, constant power is identified and turned off allowing the heat to dissipate or decay to a low power sensing mode (monitoring cutting element temperature and resistance). In step 3040, the generator "G" monitors for a change in the rate of cutter resistance (cooling) in a sensing mode to determine re-initiation of cutting element 130 and tissue contact without necessarily waiting for the cutting element 130 to cool to the temperature safe sensing zone (e.g., between about 20° C. and 60° C.). Alternatively, the generator "G" may monitor the change in temperature decay or the change in resistance decay to determine re-initiation of the cutting element with tissue. In other words, minimal power is needed in this step (passive) to determine cutter resistance/temperature.

In step 3050, cutting member 130 and tissue contact is identified by the sensing mode and, once tissue is sensed, power is ramped again to maintain temperature at about 550° C. for dissection. In step 3060, the cutting element 130 is utilized for a second or an additional open tissue dissection cycle. In step 3070, if contact between the cutting element and tissue is lost while the switch is still activated, step 3030 is repeated. In step 3080, switch 90 is released upon completion of tissue dissection and power is terminated and the cutting element 130 temperature cools over time.

Figure 10A:
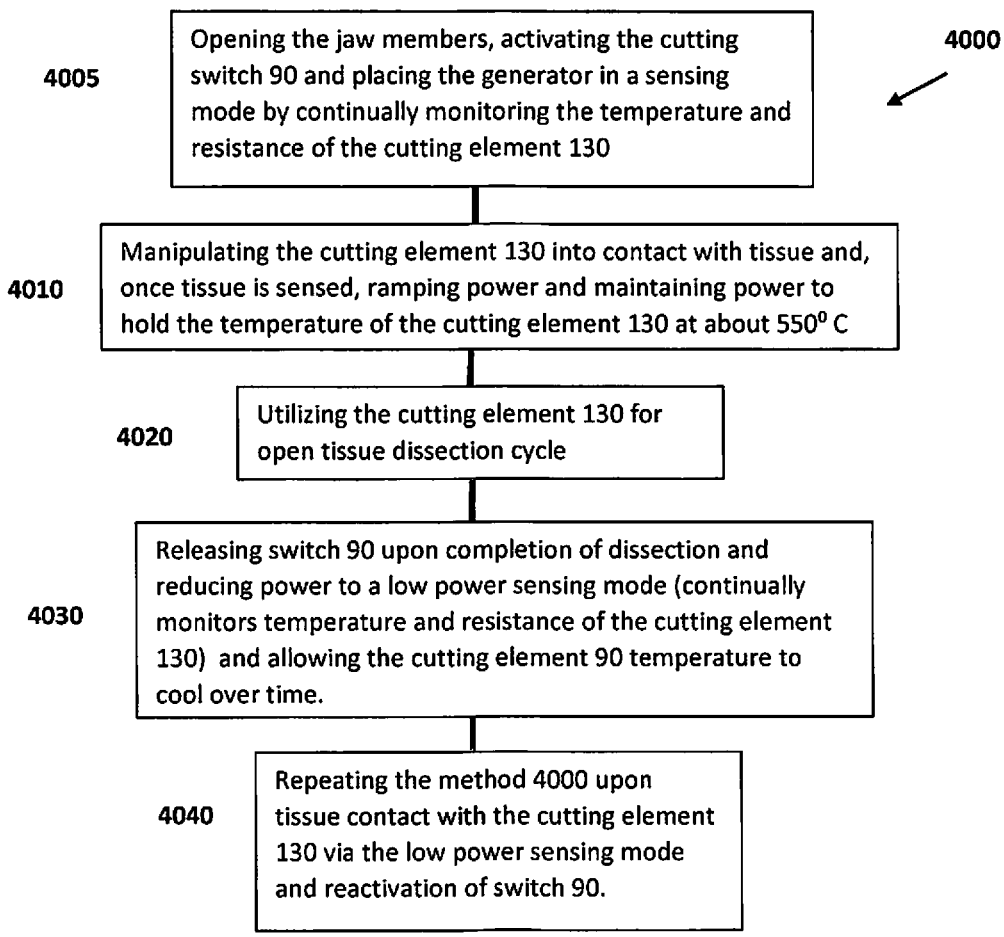
FIG. 10A is a flow chart showing a jaw open dissection cycle utilizing the initiation of cutter resistance and a continued measurement thereof to control the cutting period.
Figure 10B:
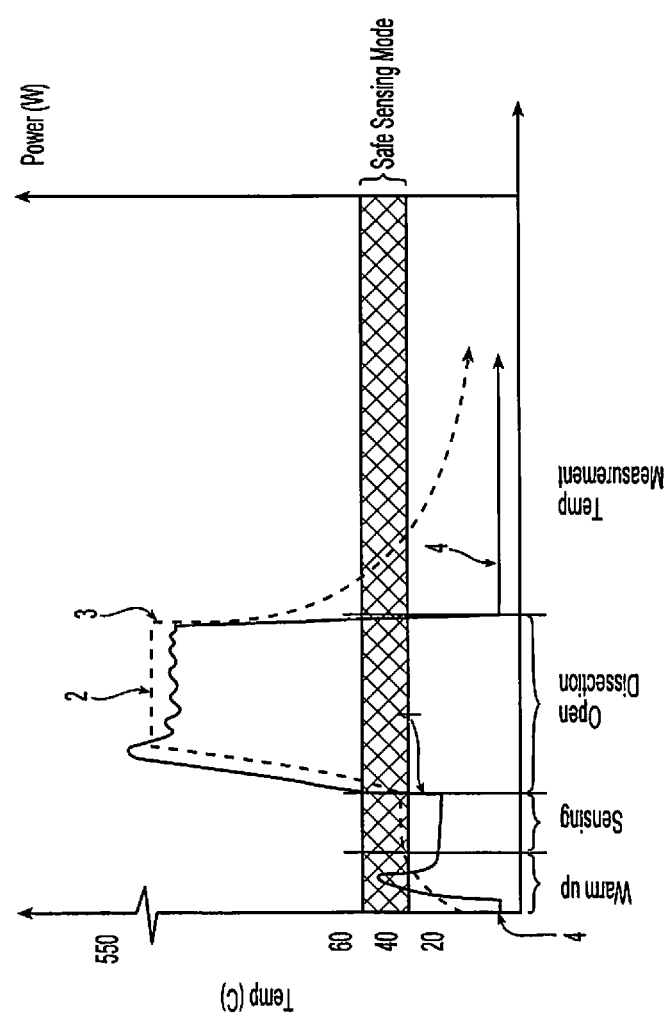
FIG. 10B is an illustrative graph corresponding to the flow chart of FIG. 10A.

FIG. 10A is a flow chart showing the various steps associated with a method 4000 for performing an open dissection cycle of tissue with constant monitoring of temperature and resistance of cutting element to regulate dissection according to another embodiment described with respect to FIGS. 6A and 6B above and FIG. 10B illustrates an accompanying graph of this method highlighting the various steps. As an initial step 4005, the jaw members, e.g., jaw members 110, 120, are opened and the cutting switch 90 is activated and placed in a sensing mode (as discussed above) by continually measuring and monitoring the temperature and resistance of the cutting element 130. In step 4010, the cutting element 130 is manipulated into contact with tissue and, once tissue is sensed, power is ramped and maintained to hold the temperature of the cutting element 130 at about 550° C. In step 4020, the cutting element 130 is utilized for open tissue dissection. In step 4030, switch 90 is released upon completion of tissue dissection and power is reduced to a low power sensing mode (continually monitors temperature and resistance of the cutting element 130) and the cutting element 130 temperature cools over time. In step 4040, the method 4000 may be repeated upon tissue contact with the cutting element 130 via the low power sensing mode and reactivation of switch 90.

As can be appreciated, this particular method 4000 continually monitors the temperature and resistance of the cutting element 130 to initiate an open dissection cycle. Moreover, the method 4000 monitors when the cutting element 130 is above 60° C. which may alleviate unintended thermal effects to tissue.

As can be appreciated, the cutter element 130 may be configured to be in a sensing mode upon activation thereof depending upon a particular purpose. Moreover, due to the proportional relationship between the resistance of the cutter element 130 and the temperature of the cutter element 130, once the resistance of the cutter element 130 is known, the temperature of the cutter element 130 would also be known at any time during the entire activation process. Still further, utilizing one or more of the above procedures and methods will reduce power consumption and would be particularly useful for battery-operated devices.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. An electrosurgical system, comprising:
   first and second jaw members each defining a tissue treating surface, the first and second jaw members pivotably coupled to one another such that at least one of the first or second jaw members is movable relative to the other from a spaced-apart position to an approximated position to grasp tissue between the tissue treating surfaces, one of the first or second jaw members including a thermal cutting element extending towards the other of the first or second jaw members; and
   a generator electrically coupled to the first and second jaw members and configured to provide electrical energy to the tissue treating surfaces to seal tissue disposed between the first and second jaw members upon activation of a first switch with the first and second jaw members disposed in the approximated position, the generator electrically coupled to the thermal cutting element and configured, upon maintained activation of a second switch with the first and second jaw members disposed in the spaced-apart position, to:
      provide power to the cutting element while tissue contact with the cutting element is not detected to maintain a pre-dissection temperature of the cutting element;
      sense a change in resistance of the cutting element to thereby detect tissue contact with the cutting element;
      ramp up the power, in response to the detection of tissue contact with the cutting element, until the cutting element reaches a dissection temperature; and
      regulate the power to maintain the temperature of the cutting element at the dissection temperature during open dissection,
   wherein the generator is further configured, upon deactivation of the second switch, to terminate the power to the cutting element.

2. The electrosurgical system according to claim 1, wherein the generator is configured to maintain a pre-dissection temperature of the cutting element in the range of about 20° C. to about 60° C.

3. The electrosurgical system according to claim 1, wherein the dissection temperature is from about 350° C. to about 550° C.

4. The electrosurgical system according to claim 1, wherein the dissection temperature is about 550° C.

5. An electrosurgical system, comprising:
   first and second jaw members each defining a tissue treating surface, the first and second jaw members pivotably coupled to one another such that at least one of the first or second jaw members is movable relative to the other from a spaced-apart position to an approximated position to grasp tissue between the tissue treating surfaces, one of the first or second jaw members including a thermal cutting element extending therefrom; and
   a generator electrically coupled to the first and second jaw members and configured to provide electrical energy to the tissue treating surfaces to seal tissue disposed between the first and second jaw members upon activation of a first switch with the first and second jaw members disposed in the approximated position, the generator electrically coupled to the thermal cutting element and configured, upon maintained activation of a second switch with the first and second jaw members are disposed in the spaced-apart position, to:
      provide power to the cutting element while tissue contact with the cutting element is not detected to maintain a pre-dissection temperature of the cutting element;
      sense a change in resistance of the cutting element to detect tissue contact with the cutting element;
      ramp up the power, in response to the detection of tissue contact with the cutting element, until the cutting element reaches a dissection temperature;
      regulate the power to maintain the temperature of the cutting element at the dissection temperature during open dissection;
      sense a change in resistance of the cutting element to detect upon loss of contact of the cutting element with tissue;
      reduce the power to the cutting element to allow the cutting element to cool to the pre-dissection temperature;
      sense a change in resistance of the cutting element to detect reinitiating contact of the cutting element with tissue;
      ramp up the power until the cutting element reaches the dissection temperature; and
      regulate the power to maintain the temperature of the cutting element at the dissection temperature during further open dissection.

6. The electrosurgical system according to claim 5, wherein the generator is configured to maintain a pre-dissection temperature of the cutting element in the range of about 20° C. to about 60° C.

7. The electrosurgical system according to claim 5, wherein the dissection temperature is from about 350° C. to about 550° C.

8. The electrosurgical system according to claim 5, wherein the dissection temperature is about 550° C.

9. The electrosurgical system according to claim 5, wherein the generator is further configured to terminate power to the cutting element upon deactivation of the second switch.

10. An electrosurgical system, comprising:
a generator configured to electrically couple to first and second jaw members and configured to provide electrical energy thereto to seal a tissue disposed between the first and second jaw members upon activation of a first switch when the first and second jaw members are disposed in an approximated position, the generator configured to electrically couple to a thermal cutting element extending from one of the first or second jaw members to provide electrical energy thereto to openly dissect tissue with the thermal cutting element upon activation of a second switch when the first and second jaw members are disposed in a spaced-apart position, the generator, upon maintained activation of the second switch, configured to:
provide power to the cutting element while tissue contact with the cutting element is not detected to maintain a pre-dissection temperature of the cutting element;
sense a change in resistance of the cutting element to detect tissue contact with the cutting element;
ramp up the power, in response to the detection of tissue contact with the cutting element, until the cutting element reaches a dissection temperature;
regulate the power to maintain the temperature of the cutting element at the dissection temperature during open dissection;
sense a change in resistance of the cutting element to detect loss of contact of the cutting element with tissue;
reduce the power to the cutting element;
sense a change in resistance of the cutting element to detect reinitiating contact of the cutting element with tissue;
ramp up the power until the cutting element reaches the dissection temperature; and
regulate the power to maintain the temperature of the cutting element at the dissection temperature during further open dissection.

11. The electrosurgical system according to claim 10, wherein the generator is configured to maintain a pre-dissection temperature of the cutting element in the range of about 20° C. to about 60° C.

12. The electrosurgical system according to claim 10, wherein the dissection temperature is from about 350° C. to about 550° C.

13. The electrosurgical system according to claim 10, wherein the dissection temperature is about 550° C.

14. The electrosurgical system according to claim 10, wherein the generator is further configured to terminate power to the cutting element upon release of the second switch.

15. An electrosurgical system, comprising:
a generator configured to electrically couple to first and second jaw members and configured to provide electrical energy thereto to seal tissue disposed between the first and second jaw members upon activation of a first switch when the first and second jaw members are disposed in an approximated position, the generator configured to electrically couple to a thermal cutting element extending from one of the first or second jaw members to provide electrical energy thereto to openly dissect tissue with the thermal cutting element upon activation of a second switch when the first and second jaw members are disposed in a spaced-apart position, the generator, upon maintained activation of the second switch, configured to:
provide power to the cutting element while tissue contact with the cutting element is not detected to maintain a pre-dissection temperature of the cutting element;
sense a change in resistance of the cutting element to detect tissue contact with the cutting element;
ramp up the power, in response to the detection of tissue contact with the cutting element, until the cutting element reaches a dissection temperature; and
regulate the power to maintain the temperature of the cutting element at the dissection temperature during open dissection,
wherein the generator is further configured, upon deactivation of the second switch, to terminate the power to the cutting element.

\* \* \* \* \*